(12) United States Patent
Scott et al.

(10) Patent No.: US 10,890,526 B2
(45) Date of Patent: *Jan. 12, 2021

(54) CLEANABLE FLAT-FACED CONDUCTIVITY SENSOR

(71) Applicant: In-Situ, Inc., Fort Collins, CO (US)

(72) Inventors: Elijah Lyle Scott, Loveland, CO (US); Duane B. McKee, Fort Collins, CO (US); Steven Collin Sewell, Fort Collins, CO (US)

(73) Assignee: In-Situ, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,495

(22) Filed: Oct. 26, 2017

(65) Prior Publication Data

US 2018/0202929 A1  Jul. 19, 2018

Related U.S. Application Data (63) Continuation of application No. 14/937,170, filed on Nov. 10, 2015, now Pat. No. 9,835,554.

(60) Provisional application No. 62/115,466, filed on Feb. 12, 2015, provisional application No. 62/115,593, filed on Feb. 12, 2015, provisional application No. 62/077,528, filed on Nov. 10, 2014.

(51) Int. Cl.
*G01N 21/53* (2006.01)
*G01N 27/07* (2006.01)

(52) U.S. Cl.
CPC .......... *G01N 21/532* (2013.01); *G01N 27/07* (2013.01); *G01N 2201/068* (2013.01)

(58) Field of Classification Search
None
See application file for complete search history.

(56) References Cited

U.S. PATENT DOCUMENTS

| | | |
|---|---|---|
| 2,769,140 A | 10/1956 | Obenshain |
| 5,099,920 A | 3/1992 | Warburton et al. |
| 5,259,452 A | 11/1993 | Wittrisch |
| 5,440,126 A | 8/1995 | Kemsley |
| D371,517 S | 7/1996 | Narayanan |
| 5,596,193 A | 1/1997 | Chutjian et al. |

(Continued)

FOREIGN PATENT DOCUMENTS

| | | |
|---|---|---|
| EP | 1851537 | 9/2013 |
| WO | WO2006/088829 | 8/2006 |
| WO | WO2014/125457 | 8/2014 |

OTHER PUBLICATIONS

Sonde Wikipedia, accessed Nov. 4, 2015.

(Continued)

*Primary Examiner* — Douglas X Rodriguez
(74) *Attorney, Agent, or Firm* — Leydig, Voit & Mayer, Ltd.

(57) ABSTRACT

Provided is a cleanable conductivity sensor and related methods having a distal sensing end in which active sensing elements are positioned and an outer fin specially configured to minimize unwanted interference without impacting the ability for automated cleaning of the distal sensing end. A rotatable wiper or brush may be periodically rotated over the distal sensing end, thereby removing unwanted biological build-up and avoiding fouling, thereby increasing the sensor deployment time without active intervention and maintenance.

42 Claims, 6 Drawing Sheets

(56) References Cited

U.S. PATENT DOCUMENTS

| | | | |
|---|---|---|---|
| 5,820,416 | A | 10/1998 | Carmichael |
| D418,073 | S | 12/1999 | Kreutzer et al. |
| 6,157,029 | A | 12/2000 | Chutjian et al. |
| 6,234,019 | B1 | 5/2001 | Caldeira |
| 6,305,944 | B1 | 10/2001 | Henry et al. |
| 6,677,861 | B1 | 1/2004 | Henry et al. |
| 6,779,383 | B2 | 8/2004 | Lizotte et al. |
| 6,798,347 | B2 | 9/2004 | Henry et al. |
| 6,928,864 | B1 | 8/2005 | Henry et al. |
| 6,938,506 | B2 | 9/2005 | Henry et al. |
| 6,943,686 | B2 | 9/2005 | Allen |
| 7,007,541 | B2 | 3/2006 | Henry et al. |
| 7,138,926 | B2 | 11/2006 | Henry et al. |
| 7,142,299 | B2 | 11/2006 | Tokhtuev et al. |
| 7,470,917 | B1 | 12/2008 | Hoang et al. |
| D616,314 | S | 5/2010 | Akomolede |
| 7,832,295 | B2 | 11/2010 | Rodriguez et al. |
| 7,900,528 | B2 | 3/2011 | Vincent |
| 8,429,952 | B1* | 4/2013 | Bringhurst ............. A01N 59/16 73/53.01 |
| 8,488,122 | B2 | 7/2013 | Dong et al. |
| 8,514,066 | B2 | 8/2013 | Harmon |
| 8,542,189 | B2 | 9/2013 | Milne et al. |
| 8,555,482 | B2 | 10/2013 | Metzger |
| 8,664,938 | B2 | 3/2014 | Palassis et al. |
| 8,797,523 | B2 | 8/2014 | Clark |
| D755,655 | S | 5/2016 | Scott et al. |
| D787,962 | S | 5/2017 | Scott et al. |
| D787,963 | S | 5/2017 | Scott et al. |
| D787,964 | S | 5/2017 | Scott et al. |
| 9,689,855 | B2 | 6/2017 | Scott et al. |
| 9,778,180 | B2 | 10/2017 | Baltz et al. |
| D803,081 | S | 11/2017 | Scott et al. |
| 9,835,554 | B2 | 12/2017 | Scott et al. |
| 2003/0117623 | A1 | 6/2003 | Tokhtuev et al. |
| 2003/0148637 | A1 | 8/2003 | Henry et al. |
| 2006/0179599 | A1 | 8/2006 | Miner et al. |
| 2007/0140921 | A1 | 6/2007 | Mitchell |
| 2008/0300821 | A1 | 12/2008 | Frank et al. |
| 2009/0158819 | A1 | 6/2009 | Vincent |
| 2010/0321046 | A1* | 12/2010 | Randall .................. G01N 27/07 324/696 |
| 2011/0005801 | A1 | 1/2011 | Oliver et al. |
| 2011/0023586 | A1 | 2/2011 | Leyer et al. |
| 2011/0273165 | A1* | 11/2011 | Palassis ................. G01D 11/00 324/149 |
| 2011/0273710 | A1 | 11/2011 | Dong et al. |
| 2012/0242993 | A1 | 9/2012 | Schick et al. |
| 2012/0262618 | A1 | 10/2012 | Weakly |
| 2012/0325018 | A1 | 12/2012 | Roth, II et al. |
| 2013/0008466 | A1 | 1/2013 | Karagoz et al. |
| 2013/0021047 | A1 | 1/2013 | Thieme et al. |
| 2013/0090789 | A1 | 4/2013 | DeDonato |
| 2014/0017143 | A1 | 1/2014 | Clark |
| 2016/0146777 | A1 | 5/2016 | McKee et al. |
| 2017/0176183 | A1 | 6/2017 | Steinbach et al. |

OTHER PUBLICATIONS

Teledyne Isco AQ700 Water Quality Multi-Parameter Sonde, 2 pages, Sep. 2013.
YSI EXO1 Multiparameter Sonde, http://www.ysi.com/productsdetail.php?EXO1-Water-Quality-Sonde-89, webpage publicly available at least as early as Oct. 2014.
YSI EXO2 Multiparameter Sonde, https://www.ysi.com/EXO2, webpage publicly available at least as early as Oct. 2014.
Hydrolab HL4 http://hydrolab.com/hydrolab-hl4-multiparameter-sonde/, webpage publicly available at least as early as May 6, 2014.
Ott Hydrolab DS5 http://www.ott.com/products/water-quality/hydrolab-ds5-multiparameter-data-sonde/, webpage publicly available at least as early as Oct. 2014.
In Situ TROLL 9500 Multiparameter Sonde, https://in-situ.com/products/water-quality-testing-equipment/troll-9500-multiparameter-sonde/, webpage publicly available at least as early as Apr. 1, 2015.
In Situ Aqua TROLL 600 Multiparameter Sonde, https://in-situ.com/products/water-quality-testing-equipment/aqua-troll-600-multiparameter-sonde/, webpage publicly available at least as early as Sep. 14, 2015.
In Situ AquaTROLL 600 Product Information, https://in-situ.com/blog/introducing-the-aqua-troll-600-water-quality-platform-2/, webpage publicly available at least as early as Sep. 21, 2015.
In Situ AquaTROLL 600 Specification Sheet, https://in-situ.com/wp-content/uploads/2015/09/Aqua_TROLL_600_Spec.pdf, webpage publicly available at least as early as Apr. 30, 2016.
In Situ Water Quality Testing Equipment Products, https://in-situ.com/product-category/water-quality-testing-equipment/, webpage publicly available at least as early as Apr. 1, 2015.
Examiner's Report for corresponding CA Application No. 163113, dated Nov. 16, 2015, 3 pages.
6-Series Multiparameter Water Quality Sondes, YSI Environmental, dated Aug. 24, 2006, 14 pages.
International Search Report with Written Opinion corresponding to International Patent Application No. PCT/US2015/059925, dated Jan. 20, 2016, 8 pages.
International Search Report with Written Opinion corresponding to International Patent Application No. PCT/US2015/059920, dated Jan. 29, 2016, 7 pages.
International Search Report and Written Opinion corresponding to International Patent Application No. PCT/US2015/059918, dated Feb. 1, 2016, 8 pages.
International Search Report with Written Opinion corresponding to International Patent Application No. PCT/US2015/059939, dated Jan. 13, 2016, 9 pages.
International Search Report and the Written Opinion of the International Searching Authority corresponding to International Patent Application No. PCT/US16/31268, dated Aug. 29, 2016.
Non-Final Rejection corresponding to U.S. Appl. No. 14/937,240, dated Feb. 9, 2017.
Notice of Allowance corresponding to U.S. Appl. No. 14/937,240, dated May 19, 2017.
Extended European Search Report, European Patent Application No. 15858742.8, dated Jun. 1, 2018, 7 pages.

* cited by examiner

CLEANABLE FLAT-FACED CONDUCTIVITY SENSOR

CROSS-REFERENCE TO RELATED APPLICATIONS

This application is a continuation of U.S. patent application Ser. No. 14/937,170, filed Nov. 10, 2015, which claims the benefit of priority of U.S. Provisional Application Ser. Nos. 62/115,466 and 62/115,593 filed Feb. 12, 2015 and 62/077,528 filed Nov. 10, 2014, all of which are hereby incorporated by reference in their entirety, to the extent not inconsistent herewith.

BACKGROUND OF INVENTION

Provided herein are water quality sensors and instruments containing multiple sensors for measuring a plurality of water-related parameters, including specifically a conductivity sensor. The sensors are uniquely configured to have an extremely high form factor so that they may be contained within a housing that minimizes dead space between sensors and within the housing, with the individual sensor ends forming a single continuous sensing surface. This provides a number of functional benefits in the field of multi-parameter sondes and related sensing methods.

Conductivity sensors generally rely on an electrode cell where certain electrodes are carefully positioned to minimize electrode fouling, which severely affects electrode performance and, therefore, conductivity sensor accuracy. Because of these concerns, it is important that the conductivity sensor be cleaned which, because of the design of conventional conductivity sensors, typically requires removal of sensor from the sensing environment and cleaning with mild detergents, fresh water and active scrubbing. This is a reflection that the conductivity sensors simply are not cleanable with a wiper while deployed. Instead, conventional conductivity sensors require frequent manual maintenance to ensure the sensor is clean and reading accurately. Accordingly, there is a need in the art for a conductivity sensor that can be automatically and reliably cleaned without having to remove the sensor from deployment.

SUMMARY OF THE INVENTION

Provided herein are conductivity sensors that are uniquely configured and shaped to facilitate cleaning of the sensor surface without removing the sensor from an operating environment while maintaining good sensor performance parameter. Accordingly, the conductivity sensors described herein are also referred to as cleanable conductivity sensors to distinguish conventional conductivity sensors that are typically enclosed to protect the electrodes and that cannot be readily cleaned without removal from the operating environment or otherwise impacting operation.

The cleanable conductivity sensors presented herein are particularly useful for embodiments wherein a plurality of sensors are provided in a multi-parameter sonde, including any of the those disclosed in U.S. Pat. App. Nos. 62/077,528 titled "Submersible multi-parameter sonde having a high sensor form factor" filed Nov. 10, 2014 and Ser. No. 29/513,888 titled "Multi-parameter sonde and sensor, sensor guard and brush portions" filed Jan. 6, 2015, each of which are hereby incorporated by reference, including for the various geometries and components described therein. The ability to include a conductivity sensor having a cleanable surface in such a multi-parameter sonde provides a number of important functional benefits. First, the sensing area of the cleanable conductivity sensor may be positioned in the same plane as every other sensor, allowing the conductivity sensor, as well as every other sensor, to be cleaned by automated movement of a wiper or brush over the sensing surfaces without affecting deployment. The sensing surfaces lying in the same plane allows the cleaning to be automatic, without any active user intervention, such as removal of the sensor from the sensing environment and/or from the sonde. This is an important aspect that facilitates achieving consistently accurate conductivity readings with minimal maintenance or active cleaning to provide for long-term deployment.

The conductivity sensor provided herein achieves these benefits by the use of a fin that extends from a planar distal sensing end having a wedge-shape, such as about one-quarter of a circle. Furthermore, a metal sensor guard positioned relative to the fin and having openings for fluid sample contact with the distal sensing end, minimizes interference effects by objects in close proximity to the sensor. These aspects related to sensor guard composition, configuration and fin geometry are more broadly referred herein as isolation-enhancing components for high-precision and robust conductivity measurement.

The conductivity sensors provided herein have fin features and can be enclosed within a metal sensor guard. Both of these aspects provide protection from interference caused by objects in close proximity to the sensor, while still allowing for ease of sensor cleaning. The advantage of the sensor described herein is that the sensor is flat and is able to be cleaned but is not affected by any external interference caused by objects in close proximity to the sensor. Without the specially configured isolation design, the sensor would suffer from significant interference due to the close proximity of external objects, causing inaccurate readings.

In an embodiment, provided is a cleanable conductivity sensor comprising a substantially planar distal sensing end. The distal sensing end comprises a vertex region, a first inner end edge extending from the vertex region to a first inner end point and a second inner end edge extending from the vertex region to a second inner end point. The first inner end edge and the second inner end edge extend in directions to define a vertex angle. An outer end edge extends between the first inner end point and the second inner end point. In this manner, each of the edges defines an outer edge shape of the distal sensing end. For straight-line end edges, the shape is a triangle. For straight-line first and second inner end edges and a curved outer end edge that is a portion of a circle, the shape will be a wedge-shape. For a vertex angle of 45°, the end shape will be one-quarter of a pie. An outer fin extends from the distal sensing end and is positioned adjacent to at least a portion of the outer end edge to define a conductivity measurement cell volume. A plurality of electrodes having a distal end positioned at or proximate to the distal sensing end and between the outer fin and the vertex region measure conductivity in the conductivity measurement cell volume.

Any of the cleanable conductivity sensors may further comprise an inner fin extending from the distal sensing end, wherein the outer fin and the inner fin are separated from each other by a fin separation distance to define the conductivity measurement cell volume. The conductivity measurement cell volume may be defined as the surface area of the distal sensing end corresponding to between the vertex region or the inner fin, when present, and an inward-facing surface of the outer fin multiplied by the fin height. For inner and outer fins of different heights, the height may be calculated as an average of the inner and outer fin height.

In an aspect, the outer fin has a fin outer-facing surface positioned within 3 mm of the outer end edge. In an aspect, the fin outer-facing surface extends continuously from at least a portion of the outer end edge to form a continuous outer-facing surface.

The first inner end edge and the second inner end edge each extend a radial distance from the vertex, the radial distance selected from a range that is greater than or equal to 1 cm and less than or equal to 20 cm. In an aspect, the length of the inner edges equal are equal each other and are between about 1.6 cm and 2 cm, or is 1.8 cm. In an aspect, the lengths of the inner edges are not equal to each other and are independently selected as greater than or equal to 1 cm and less than or equal to 20 cm.

In an aspect, the outer end edge is curved, such as having a curvature that is a portion of a circle.

In an aspect, the vertex angle is greater than or equal to 30° and less than or equal to 180°, including about or equal to 45°. In this manner, the cleanable conductivity sensor may be used in combination with three other sensors, each having a 45° vertex angle, and the entire plurality of sensors enclosed with a sensor guard having a circular cross-section and a less than about 1 mm separation distance between the curved outer surfaces of the sensor and an inner surface of the sensor guard.

In an aspect, the distal sensing end has a cleanable surface area that is greater than or equal to 1 cm$^2$ and less than or equal to 20 cm$^2$. In an aspect, the cleanable surface area is between about 1 cm$^2$ and 3 cm$^2$, or about 2.1 cm$^2$.

For any of the sensors provided herein, the vertex region may comprise a notch configured to receive a rotatable drive shaft in a tight-fit configuration. In this manner, the distal sensing end of the sensor may have an inner radius corresponding to the notch edge and an outer radius corresponding to the curved outer end edge, such that the difference in radii is about 1.8 cm, including an about 2.0 cm outer radius and 2 mm or smaller inner radius. The notch, when combined with other sensors contained in similarly constructed sensor housing, provides a passage that can tightly accommodate a rotatable shaft that rotates a wiper attached to a distal end of the shaft to clean the sensor surfaces, including the conductivity sensor surface.

In an aspect, the outer fin and the inner fin have a laterally-directed shape that corresponds to a shape of the outer end edge, such as a curved shape that is a portion of a circle. The curved shape may be quantified in terms of a radius of curvature, such as a radius of curvature that is greater than or equal to 1 cm and less than or equal to 20 cm and the vertex angle is 45°.

In an embodiment, the distal sensing end has a surface shape that is a portion of a circle having a ratio of cleanable surface area to distal sensing end surface area that is greater than or equal to 70%, 80%, or 90%. In an aspect, the cleanable area is defined by the surface area that is between the outer and inner fins. In an aspect, the cleanable surface area corresponds to the surface area over which a wiper in physical contact with the distal sensing end rotates.

The outer fin dimension may be defined in terms of a desired functional performance parameter, such as dimension and/or shape selected to provide an electric field in the conductivity measurement cell volume that is independent of a sensor guard position that encloses the distal sensing end. In this manner, the electric field is independent of the sensor guard orientation with respect to position of passages through the sensor guard relative to the conductivity measurement cell volume.

In an embodiment, the electrodes of the cleanable conductivity sensor are separated from an inner surface of the outer fin by a fin-electrode separation distance. This separation may be defined in terms of an absolute value, such as between 0.2 cm and 1.5 cm, or between 0.2 cm and 0.5 cm, or about 0.3 cm. Alternatively, the separation may be described in terms of a ratio of the outer fin height to the fin-electrode separation distance, such as a ratio between outer fin height and electrode separation that is greater than or equal to 2.4. In an embodiment the fins are described in terms of one or more of fin height, fin surface area that defines one surface of the conductivity measurement cell volume, and fin thickness. In an aspect, the fin heights are between about 0.25 cm and 1 cm, or between 0.5 cm and 0.8 cm. The fin surface area is defined, for a 45° pie-shaped sensor, as the product of the fin height and $0.25\pi*2r$, where r is the distance from the vertex region to the position of the outer fin (for outer fin surface area) or the inner fin (for inner fin surface area). In an aspect, the fin is characterized as being thin-walled. In an aspect, a thin wall has a thickness that is less than 3 mm, less than 2 mm, or less than 1 mm.

In an aspect, the outer fin height is greater than or equal to 1 mm and less than or equal to 5 cm, or between 5 mm and 10 mm, or between 7.0 mm and 8.0 mm. In an aspect the outer fin height is equal to the inner fin height. Alternatively, the outer fin height is greater than the inner fin height. In an aspect, the outer fin surface area is greater than or equal to 2 cm$^2$ and less than or equal to 8 cm$^2$. In an aspect, the inner fin surface area is greater than or equal to 0.3 cm$^2$ and less than or equal to 2 cm$^2$.

In an embodiment, the fin separation distance is greater than or equal to 0.5 cm and less than a length of the first or second inner end edge.

Any of the cleanable conductivity sensors described herein may further comprise a sensor guard having a plurality of openings to surround the distal sensing end and the outer fin. In this context, surround refers to a protective enclosure around the distal sensing end, but in a manner that permits fluid contact with the fluid environment in which the sensor is immersed. This fluid contact can be accomplished by a range of means, so long as protection of the distal sensing end from unwanted physical contact and fluid access is maintained. For example, the sensor guard may have a mesh-type geometry. Alternatively, the guard may be formed of a solid material having a plurality fluid passages disposed therein. In an embodiment, the guard is formed of a metal material, such as a metal material to minimize unwanted electrical interference from an object positioned outside the sensor In an aspect, the first fin is adjacent to an inner surface of the sensor guard and the sensor guard comprises one or more fluid sample openings for fluid sample introduction from a fluid environment outside the sensor guard to the conductivity measurement cell volume. For example, the guard separation distance between the outer fin and the sensor guard inner surface may provide a tight-fit that substantially prevents biological growth between the outer fin and the sensor guard inner surface. In an aspect, the guard separation distance is less than 1 mm or less than 0.8 mm.

In an aspect, the cleanable conductivity sensor has a ratio of conductivity measurement cell volume to a sensor sensing volume that is greater than or equal to 0.0001 and less than or equal to 0.1, including for a sensor sensing volume that is about 3.1 inches$^3$ and a conductivity measurement cell of about 0.1 inches$^3$.

The cleanable conductivity sensors described herein may be further described in terms of one or more beneficial functional parameters. For example, the cleanable conductivity sensors may be described in terms of having a long-term, high-fidelity conductivity sensing without having to remove the cleanable conductivity sensor from a measurement environment and/or without active maintenance. This is achieved by the special geometry of the sensor distal sensing end that is generally flat, except for the specially configured outer fin that extends from the distal end at or adjacent to the outer surface edge or electrodes that extend slightly. Furthermore, crevasses or other recess features are avoided that otherwise are difficult to clean with a brush so that biological growth can build-up, resulting in fouling and a need for sonde maintenance The specially configured sensor ends provided herein, however, allows for reliable automated cleaning with a wiper or brush that may be automatically rotated over the distal sensor surface to ensure high-performance of the electrodes in the conductivity sensors are maintained by removal of contaminating or fouling substances. In contrast, conventional conductivity sensors need to be either removed from the environment for cleaning or other active maintenance such as cleaning by an individual. In an aspect, the cleanable conductivity sensor may have a measurement accuracy that is within 0.5% for an operating time of at least six months without active maintenance or removal of the sensor from an operating environment.

The outer fin can be further described as minimizing conductivity interference from objects located outside the conductivity measurement cell volume. In an aspect, the outer fin may decrease conductivity interference by at least 50% compared to an equivalent cleanable conductivity sensor without the outer fin.

In an aspect, the plurality of electrodes are open to a sensor sensing volume, such as a sensor sensing volume that is defined by the inner surfaces of the sensor guard. The conductivity measurement cell volume is a correspondingly sub-volume of the sensor sensing volume. Fluid surrounding the sensor guard is then in fluidic contact with the sensor sensing volume via openings or passages through the sensor guard.

Any of the plurality of electrodes of the cleanable conductivity sensor may comprise two drive electrodes and two sensing electrodes. Each of the electrodes may have a distal end that terminates coincident with or proximal to the planar distal sensing end. In this manner, the generally planar configuration of the distal sensing end is not substantially disturbed. Similarly, the cleanable conductivity sensor may further comprise a temperature sensor having a temperature sensing surface that is coincident with or proximal to the distal sensing end. Coincident refers to an end having a distal end that corresponds to the plane formed by the distal sensing end. Proximal refers to an end that is near the plane formed by the distal sensing end, but that does not significantly adversely impact the ability to clean the surface, such as with a wiper that is capable of cleaning the surface to maintain a desired measurement accuracy, such as within 1%, or within 0.5% over time. In an aspect, proximal may be within a characteristic dimension of the electrode or temperature sensor, such as a diameter or thickness, or may be expressed in terms of an absolute value, such as within about 1.5 mm or within 1 mm, of the distal sensing surface.

The cleanable conductivity sensor may have a sensor sensing volume defined by an inner surface of the sensor guard that encloses the cleanable conductivity sensor, the sensor sensing volume greater than or equal to 0.5 mL and less than or equal to 100 mL. The conductivity measurement cell volume may be defined by an outer fin separation distance from the vertex region, an outer fin height, and a length of the outer fin height.

Any of the cleanable conductivity sensors are useful as part of a multi-parameter sonde. The cleanable conductivity sensor may further comprise a first flat-faced inner surface and a second flat-faced inner surface that terminate at the first and second inner end edge, respectively. The distal sensing end may form a portion of a circle. For example, for four equivalently shaped sensors, including one of the instantly described conductivity sensors, the distal sensing end may be a one-quarter circle. One or more additional sensors may be similarly shaped so that each additional sensor has a distal sensing surface, a first flat-faced inner surface and a second flat-faced inner surface extending from a vertex region that comprises a notch. A curved outer surface may extend between the one or more additional sensors first flat-faced inner surface and the second flat-faced inner surface. In combination, the conductivity sensor and the one or more additional sensors form a single continuous sensing surface having a circular outer circumference in a single plane with a central orifice comprising the notches of the vertex regions. A rotatable drive shaft is positioned in the central orifice and a wiper operably connected to the rotatable drive shaft and in rotatable contact with the single continuous sensing surface for cleaning a sensor portion of the single continuous sensing surface during use and a cleanable surface area of the cleanable conductivity sensor. A sensor guard having a sensor volume contains the continuous sensing surface and wiper within and adjacent to the sensor volume.

In an embodiment, the cleanable conductivity sensor is described further in terms of the wiper, such as a wiper comprising a central body having a downward-facing surface and an upward facing surface. A lower wiper is connected to the downward-facing surface for rotatably contacting the sensor portion of the single continuous sensing surface. An upper wiper is connected to the upward-facing surface for rotatably contacting a downward-facing surface of the sensor guard. The lower wiper has a lateral dimension that corresponds to an outer fin separation distance and the upper wiper has a lateral dimension to rotatably contact substantially all of the sensor guard downward-facing surface.

The one or more additional sensors may be any sensor of use in the application of interest, such as a sensor selected from the group consisting of: a dissolved oxygen sensor, oxygen-reduction potential sensor, pH sensor, pressure sensor, turbidity sensor, ion sensor, temperature sensor, and sensor blank.

Also provided herein are methods of making or using any of the cleanable conductivity sensors described herein. In an aspect, the method of making a cleanable conductivity sensor comprises the steps of enclosing a plurality of electrodes in a wedge-shaped sensor housing having a substantially planar distal end that is coincident with or proximate to a distal end of each of the plurality of electrodes. The wedge-shaped sensor housing has a curved outer surface that corresponds to a portion of a circle. An outer fin is positioned adjacent to the curved outer surface and extends along at least a portion of a lateral length of the curved outer surface. The outer fin extends from the sensor housing distal end by an outer fin height. Optionally, an inner fin is positioned in a parallel configuration to the outer fin and separated from the outer fin by a fin separation distance, wherein the plurality of electrode distal ends are positioned between the outer fin and the vertex region or, when present, the inner fin. The inner fin has a lateral length that is less than a lateral length of the outer fin, wherein the inner fin extends from the sensor housing distal end by an inner fin height. A rotatable wiper having a cleaning surface is provided in rotatable contact with the sensor housing distal end and between the outer fin and the inner fin, if present, or the vertex region.

In an aspect, the rotatable wiper is automatically engaged to clean the sensor housing distal end between the first fin and the second fin by rotation of the cleaning surface relative to the sensor housing distal end. This is in contrast to active cleaning, requiring an action on the part of a user to clean the sensor, such as by removal of the sensor housing portion from the device or interrupting of sensor operation.

Also provided herein is a method of making an accurate conductivity measurement in a liquid comprising the steps of: providing a multi-parameter sonde comprising any of the conductivity sensors described herein and at least one additional sensor, wherein active sensing elements of the sensors are coincident with a single continuous distal sensing surface. A wiper is rotably connected to the single continuous distal sensing surface, including the conductivity sensor portion between an outer fin and an inner fin, if present, or a vertex region. The single continuous distal sensing surface and the wiper are enclosed within a sensor guard having one or more openings. The multi-parameter sonde is inserted into a liquid environment and the wiper periodically rotated over the single continuous distal sensing surface to clean the single continuous distal sensing surface without removing the multi-parameter sonde from the liquid environment. A conductivity parameter is measured with the conductivity sensor to make an accurate conductivity reading in a liquid.

The method may further comprise the step of storing the wiper in a stored position that does not interfere with a sensor reading of the conductivity sensor or any of the other sensors.

In an aspect, conductivity sensor performance is independent of position of the one or more openings through the sensor relative to the conductivity sensor.

The periodically rotating step may be automated, such as to occur by a user-defined time or in response to a fouling signal from the multi-parameter sonde.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Cleanable", in the context of the instantly described cleanable conductivity sensors, refers to the ability to automatically clean the sensor to maintain good conductivity sensor performance without impacting ongoing sensor operation. Accordingly, cleanable does not simply include those conductivity sensors that must be removed from operation in order to clean the conductivity sensor so as to maintain tolerable sensor performance. Similarly, cleanable does not include active actions on the part of a person to access and clean by hand. Instead, the special configurations provided herein permit automation of efficient and robust conductivity sensor cleaning without having to remove the sensor from an operating environment or otherwise actively intervene.

In the context of a distal sensing end, "substantially planar" refers to a surface having a well-defined plane, but that my contain portions therein that extend out of the plane. For example, a sensor housing distal end may form a single plane, but have passages through which components pass, such as electrodes and temperature sensors. Those components may be flush with the distal sensing end plane. The invention, however, can accommodate deviations of those components from the plane, such as an about 2 mm or less, 1 mm or less, or less than 0.5 mm extension into or out of the plane, so long as the cleanability aspect is minimal and the attendant loss in accuracy during long-term use is avoided. The electrodes and/or temperature sensor may extend out of the planar surface, so as to ensure there is not a recess into the surface. Such recesses are preferably avoided as having a tendency to be hard to clean, so that biological growth and corresponding fouling may occur and/or as places that air pockets can settle, potentially adversely interfering with sensor measurement. Accordingly, the electrodes having a distal end positioned at the distal sensing end encompass electrode tips that extend out of the distal end surface, such as extending a distance that is greater than 0 mm to less than about 2 mm, or between 0.5 mm and 1.5 mm. To reflect this tolerance, the electrode tips may be referred to as having distal ends that are "adjacent" or "proximate" to the distal sensing end, or that is within 2 mm of the distal end surface. Because the footprint of the electrodes is much smaller than the area of the distal sensing end, the surface as a whole, even with the extending electrodes, remains fairly characterized as substantially planar.

"Sonde" refers to a water quality monitoring instrument. "Multi-parameter" refers to a sonde having multiple independent separate sensors for providing multiple water parameter values.

"Independent sensors" refers to the ability to insert or remove a sensor without affecting other sensors. For example, one of the sensors may be removed and replaced with a sensor blank. Similarly, a user in the field may simply remove one independent sensor and replace it with another of the same or different sensor, without affecting the other sensors. "Sensor blank" refers to an equivalently shaped object that is used in place of a sensor. It is useful if the user does not need or have a sensor to connect to the base so as to fully fill the sensor guard.

The devices provided herein are compatible with a range of sensors, including sensors that measure conductivity, dissolved oxygen (DO), oxygen-reduction potential (ORP), pH, pressure, depth, level, turbidity, ion selective electrodes for various ions, such as nitrate, ammonium and chloride, temperature.

"Continuous distal sensing surface" refers to a plurality of independent sensors that are placed adjacent to each other to form a single surface that, to the naked eye or casual observer, appears continuous. The invention, however, does tolerate some separation distance, preferably less than 2 mm, less than 1 mm, or less than 0.5 mm. Tight-fit and tightly held are used herein in a similar manner, to reflect the minimal space between adjacent surfaces, in contrast to conventional systems that have rather large gaps and attendant large void volumes. Accordingly, adjacent distal sensing surfaces that "substantially contact" each other may refer to an open surface area between sensors that is less than 5%, or less than 1% of the surface area of the continuous distal sensing surface.

Unless defined otherwise, "substantially" refers to a value that is within at least 20%, within at least 10%, or within at least 5% of a desired or true value. Substantially, accordingly, includes a value that matches a desired value.

"Operably connected" refers to a configuration of elements, wherein an action or reaction of one element affects another element, but in a manner that preserves each element's functionality. For example, a wiper operably connected to a center support refers to the ability to move the wiper without impacting the functionality of the center support that supports the sensors in an interlocking configuration.

"Releasably connected" or "releasably connects" refers to a configuration of elements, wherein the elements can be temporarily and reliably connected to each other and, as desired, removed from each other without adversely impacting the functionality of other elements of the device.

"Void volume" refers to the empty space between sensors and between sensors and a side-wall of a cover or a sensor guard. Conventional multi-parameter sondes have void volumes that are relatively large with sufficient separation distances that biological growth can become a significant problem. The low void volumes of the instant devices reflect a tight fit between all adjacent sensors and the side wall of the sensor guard, with separation distances so small that biological growth is substantially constrained. In this aspect, "substantially constrained" refers to minimal growth that does not affect long-term sensor performance. For example, there may be biological growth not observable to the naked eye, or the observable growth is so minor that there is no detectable drop-off in a sensor performance. Void volume may be expressed in terms of a fraction or percentage of guard's sensor receiving volume.

In contrast, "sample volume" or "sensor volume" refers to that part of the system in which fluid is desirably located, such as for water parameter measure or sensor storage. In an aspect, this volume is between about 20 mL and 100 mL, or about 40 mL to 50 mL, depending on sensor size, for example. In comparison, conventional sondes may have up to around double, triple or an order of magnitude volumes, as a result of the substantially large void volume that requires filling so as to ensure the distal sensing surfaces are covered with liquid.

"Conductivity measurement cell volume" refers to a portion of the sensor volume in which conductivity is measured, wherein for objects outside the conductivity measurement cell volume, their effect on conductivity is negligible.

A multi-parameter sonde may have pie shaped sensors that fill the entire sensor space of the multi-parameter sonde. Other sondes, in contrast, use mostly round sensors that have open space between sensors.

The pie shape reduces the volume of liquid that surrounds the sensor which has a certain advantages. First, a small volume of water in a flow cell leads to faster testing results during low flow sampling, such as from well water. Second, less calibration solution is required to calibrate and instrument, which can save significant amount of money as some calibration fluids cost several hundred dollars a liter.

In addition, pie shaped sensors are easier to clean after long deployments because the sensors are in direct contact with each other, which reduces the surface area in direct contact with biologically active water that grow algae and other biological growth. Other multi-parameter sondes have sensors that are spread out and the biological growth has to be cleaned in between sensors. The sondes provided herein do not require cleaning in between sensors, even after extended periods of use, such as on the order of weeks or months.

Particularly relevant herein, is a cleanable conductivity sensor that can be used, as desired, in a multi-parameter sonde.

Figure 1A:
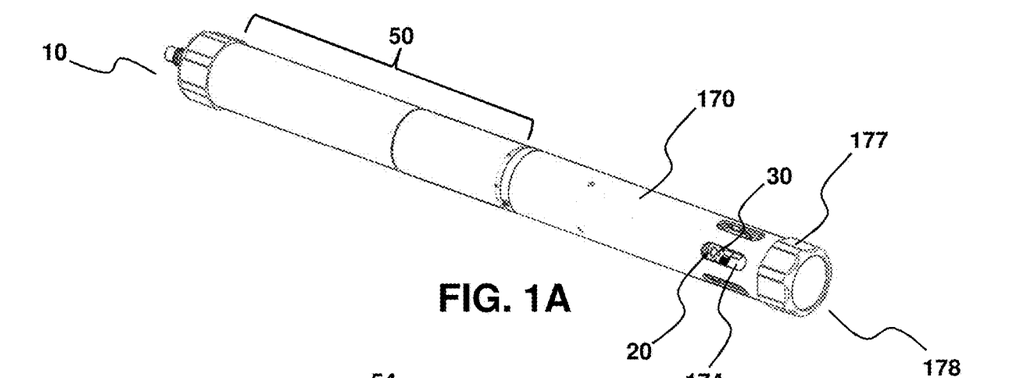
FIG. 1A is a top perspective view of a multi-parameter sonde with a sensor guard in a sensor guard configuration to enclose a plurality of sensors, including a cleanable conductivity sensor and wiper within a sensor volume.
Figure 1B:
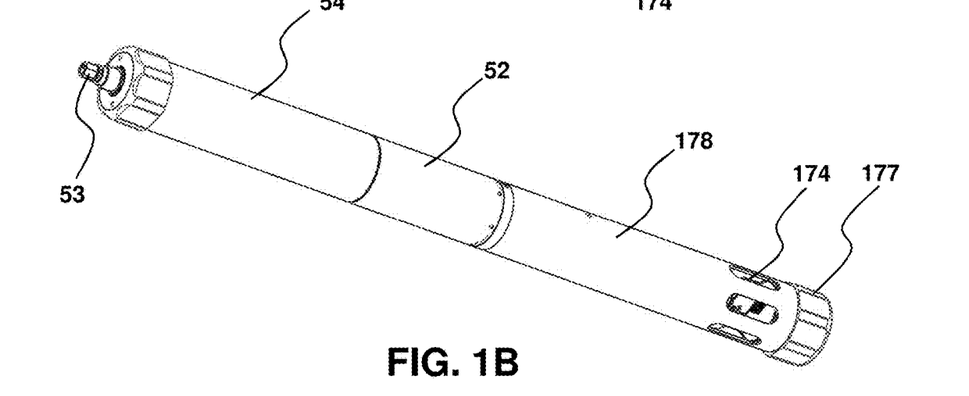
FIG. 1B is a bottom perspective view thereof.
Figure 1C:
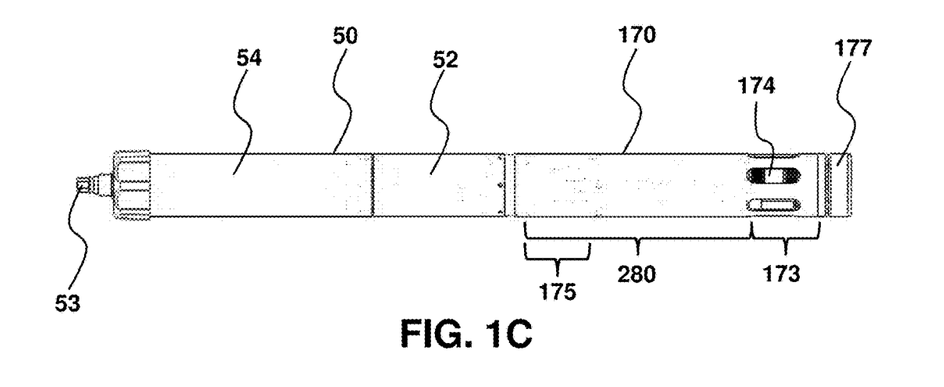
FIG. 1C is a side view thereof.

Referring to FIG. 1A-1C, in a fully assembled configuration ready for sensing in a submerged environment, the multi-parameter sonde 10 has a plurality of independent sensors 20 disposed within a sensor guard 170, including a cleanable conductivity sensor. The sonde is shown in a sensor guard configuration 178 in that the sensing end 173 having a plurality of fluid openings 174 is aligned with the distal sensing surfaces 30 of sensors 20. Each opening 174 may be split into two or more openings, such as a pair of openings that are separated by a separation distance, including a separation distance of between about 2 mm to 2 cm. Covering end 175 is positioned in a proximal position, relative to the sensing end 173 of the sensor guard. The sensing end corresponds to the sample volume. The sensor guard is open-ended, with one end, the proximal end, closed via the connection with the base 50 and the other end, the distal end, closed via the cap 177. Sensor receiving volume 280 corresponds to the portion of the sensor guard 170 in which the sensors extend and, therefore, depends on the sensor longitudinal length. The volume of sensing volume 173 may be about 40 mL-50 mL, or about 46 mL.

The base 50 may further comprise a display portion 52 for indicating sonde and sensor status, and a base end 54 for containing other sonde components, such as power supply, electronics and external connection port 53.

Figure 2:
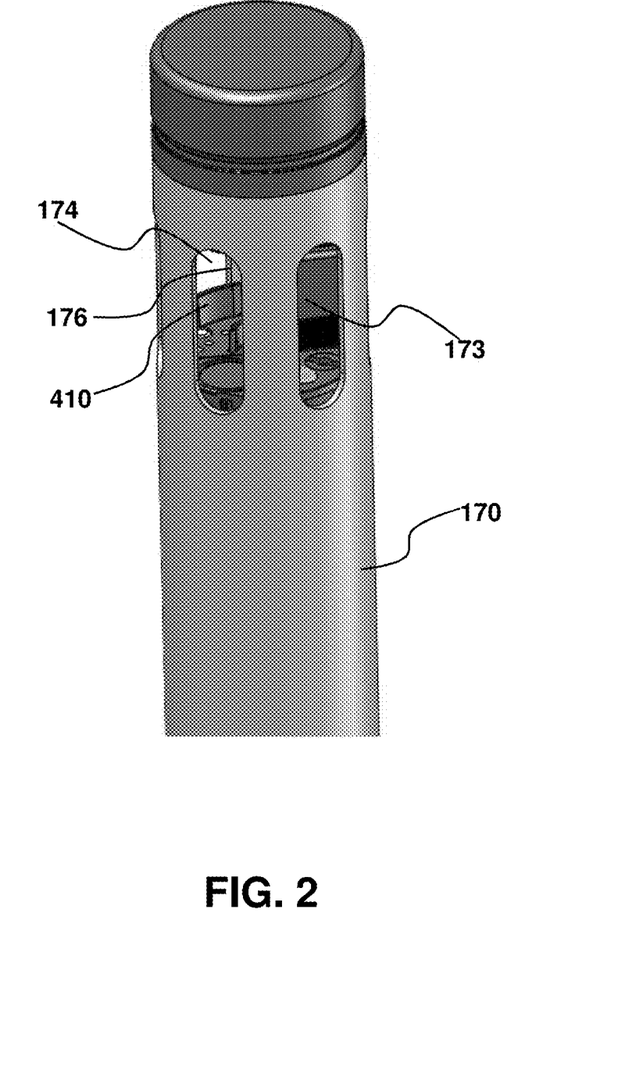
FIG. 2 is a close up view of the sensor guard and passages that enclose the sensor distal sensing end and wiper, while permitting fluid access to the sensor volume and conductivity sensor volume of the cleanable conductivity sensor. The outer fin of the cleanable conductivity sensor is positioned adjacent to a rear-facing passage.

FIG. 2 is a close-up view of the sensor guard 170, guard passages 174, and distal sensing end, including outer fin 410, is observable through the guard passages. There is little separation distance between the inner-facing surface 176 of the sensor guard and the outer fin 410, and outer-facing surface of the sensors.

Figure 3A:
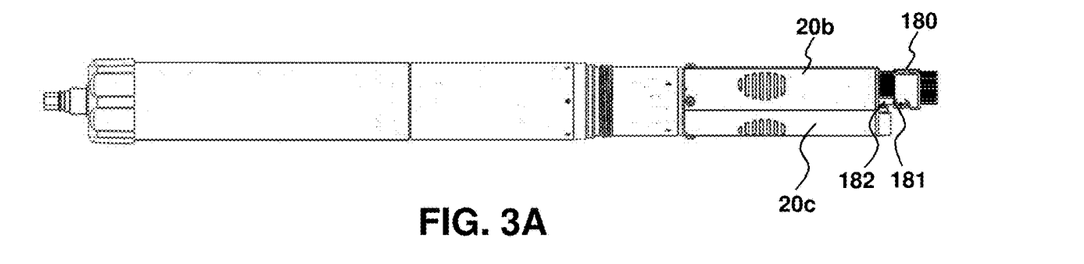
FIG. 3A is a side view of the multi-parameter sonde of FIG. 1A with the sensor guard removed to show the plurality of sensors that are in an adjacent configuration and a cleaning brush that are normally confined within a sensor guard during use.
Figure 3B:
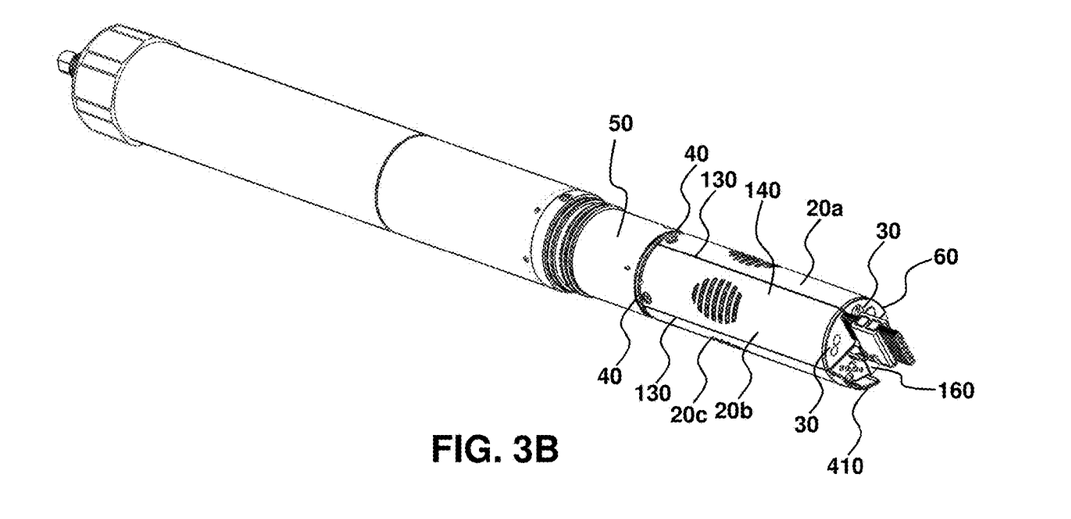
FIG. 3B is a perspective view thereof showing the cleanable conductivity sensor with outer and inner fins relative to the cleaning brush.

A multi-parameter sonde with the sensor guard 170 removed is illustrated in FIG. 3A-3B. Plurality of independent sensors 20 (20a 20b 20c 20d) (shown as sensor blank 160)) each have a distal sensing surface 30 and a proximal end 40 connected to the base 50. Cleanable conductivity sensor corresponds to sensor 20c, as shown by outer fin 410. As shown in FIG. 3B, adjacent distal sensing surfaces contact each other to form a continuous distal sensing surface 60 having a substantially planar surface. The fitting between the independent sensors is so tight, that the outer surface cross-section visually appears as a solid circle. Because the fit between all the adjacent sensors is close or tight, the sensors are also referred herein as having a high "form factor", with minimal void volume or dead space between the sensors that extend from the base 50 and proximal end 40 to the distal sensing surface 30 and, in combination, the continuous distal sensing surface 60. Also illustrated is a wiper 180 that is connected to a distal end 181 of a drive shaft 182.

The sensors may generally be described as "pie shaped", and can have an interlocking feature that holds the sensors together. The interlocking feature can be a tongue and grove design that holds all the sensors to the center support that is operably connected to the wiper. This has a number of benefits, including enhancing impact resistance as the interlocking protects the sensors during a drop or impact in situations where the sensor guard is not installed. It also holds the sensors tightly together and makes sensor guard installation easier. Without the interlocking feature the sensors tend to splay out and have to be pushed together to install the tightly fitting sensor guard.

Figure 4:
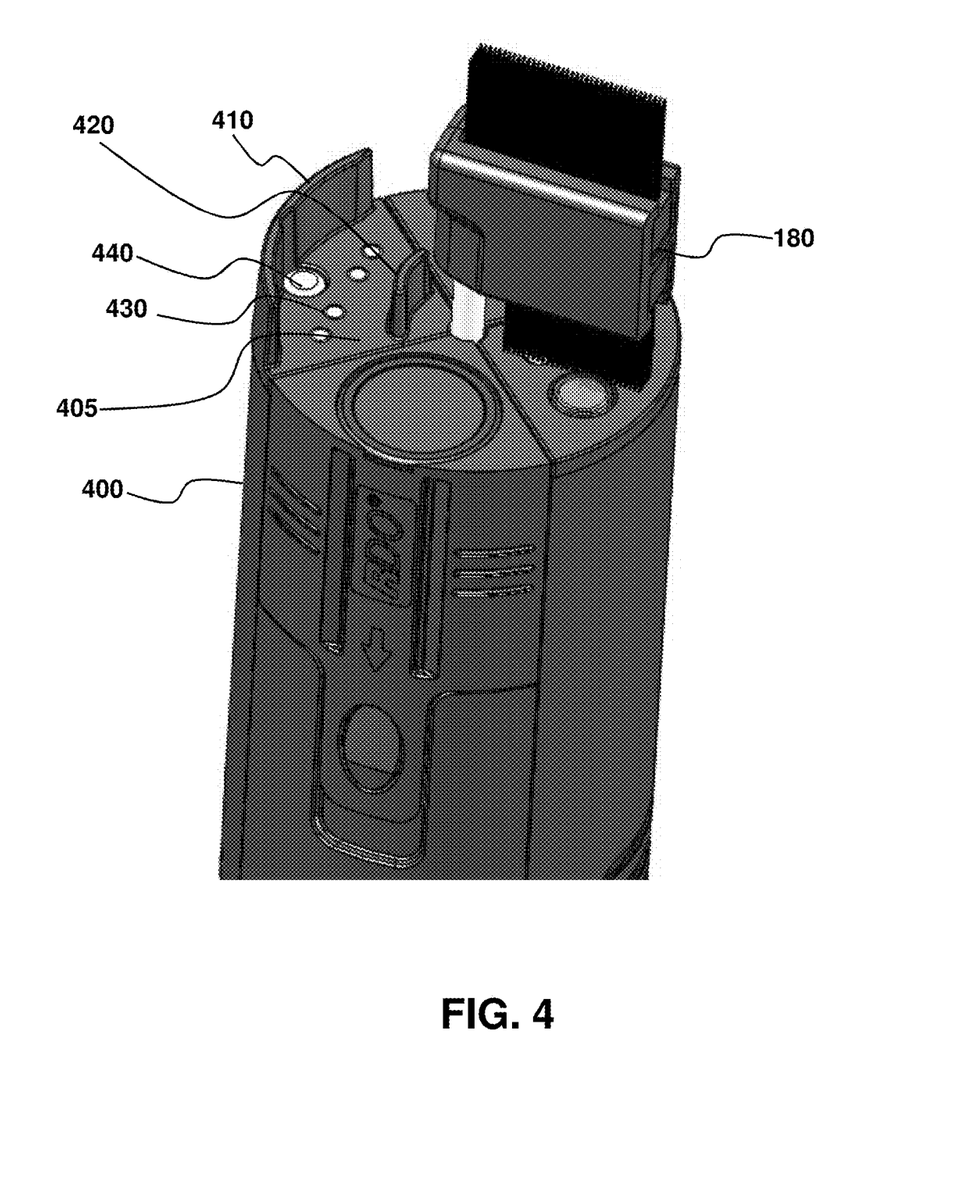
FIG. 4 is a close-up view of the distal sensing surfaces of FIG. 3B, including the distal sensing end of the cleanable conductivity sensor, to show the relative positions of the fins, electrodes, temperature sensor, rotatable wiper, and drive shaft.

A close-up view of the cleanable conductivity sensor 400 within a multi-parameter sonde is provided in FIG. 4. Connected to the substantially planar distal sensing end 405 is outer fin 410 and inner fin 420, and positioned therebetween are a plurality of electrodes having a distal end 430 positioned between the outer fin 410 and the inner fin 420. Also illustrated are a temperature sensor 440 and a wiper 180 that is used to clean at least the sensing area of the cleanable conductivity sensor.

The instant single continuous sensing surface allows a sensor cleaning brush to wipe on a flat even surface, without open spaces between sensors. The brushes and wipers are more effective at cleaning because there is not deflection around the sensors due to the space between probes, as is currently found with conventional multi-parameter sondes on the market.

Figure 5:
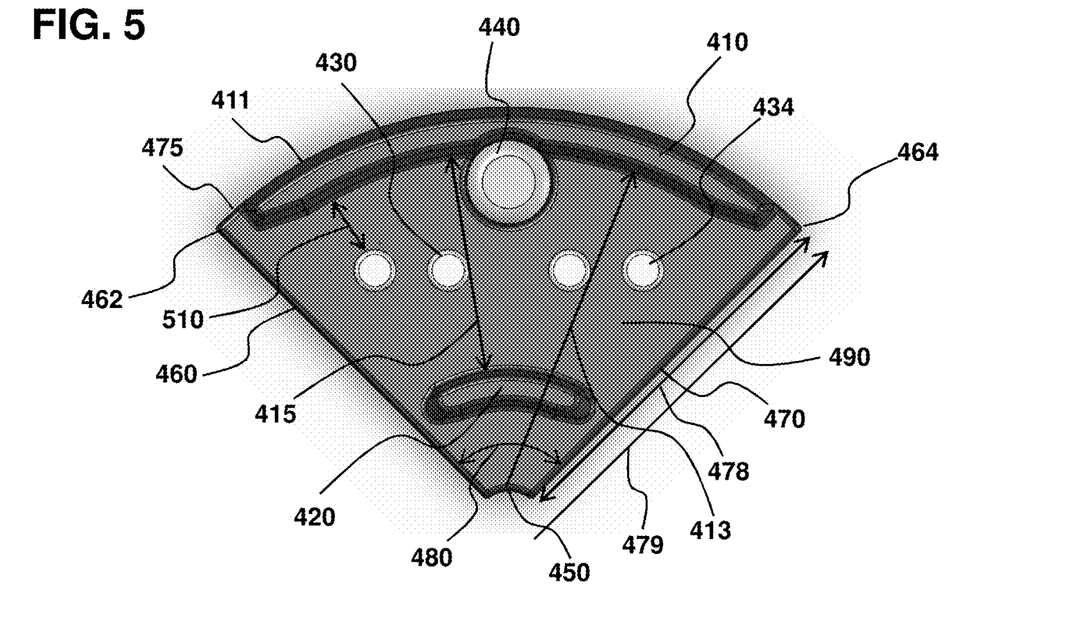
FIG. 5 is a top-view of the cleanable conductivity sensor.

FIG. 5 is a top view of the cleanable conductivity sensor 400 of FIG. 4 removed from the other sensors. The outer fin is separated from the inner fin by a fin separation distance 415. The circumference of the distal sensing end is defined by a vertex region 450, first inner edge 460, second inner edge 470 and outer edge 475. The inner edges 450 460 extend from the vertex region 450 to first inner end point 462 and second inner end point 464, respectively. The outer edge extends between inner end points 462 464. Length of the inner edge 470 is defined by arrow 478 and distance of inner end point 464 from the vertex is defined by arrow 479. The directions of the inner edges relative to each other define a vertex angle 480. Each of four electrodes 430 and temperature sensor 440 are positioned in a conductivity measurement cell volume 490 to ensure accurate conductivity sensing that compensates for temperature and minimizes external interference. The outer fin 410 has an outer-facing surface 411 that can extend from the outer facing surface 475 (see, e.g., FIG. 6). The outer fin extends a radial distance 413 from the vertex.

The cleanable surface area is defined as that portion of the sensor surface that is between the fins, as indicated by fin separation distance 415 and that continuously extends in a circular rotation between inner edges 460 470.

The fin electrode separation distance 510 may refer to an average separation distance for the electrodes. The electrodes may be drive electrodes 432 and sensing electrodes 434.

Figure 6:
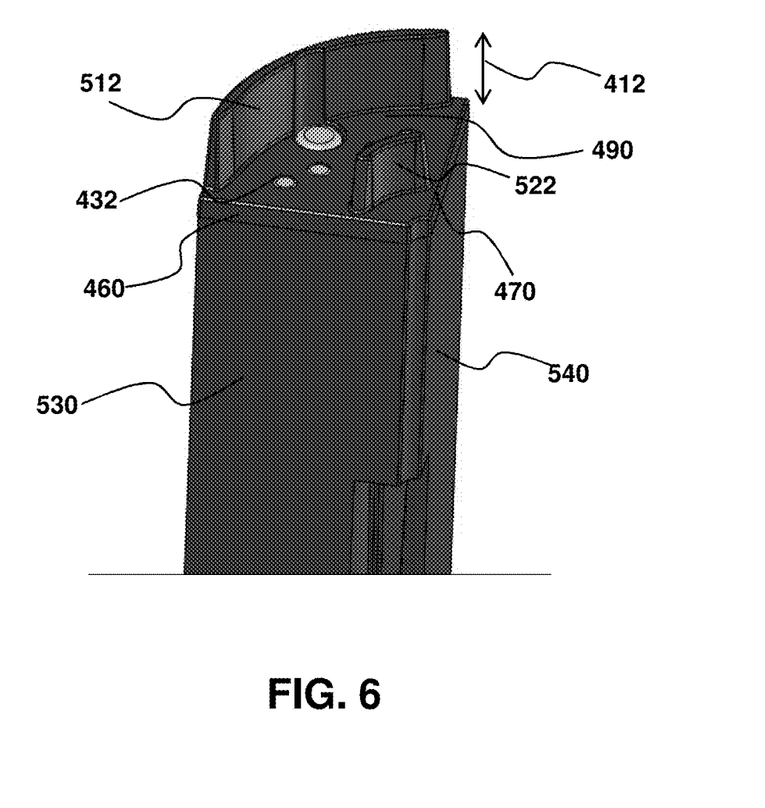
FIG. 6 is a perspective view of the cleanable conductivity sensor of FIG. 5.

FIG. 6 is a perspective view of the cleanable conductivity sensor of FIG. 5 and better illustrates the conductivity measurement cell volume 490 between the fins 410 and 420 and the planar distal sensing end in which the electrodes and temperature sensor distal ends are positioned. Outer fin height is illustrated by arrow 412. Inner fin height is similarly defined. The outer fin and inner fin may have surface areas 512 and 522, respectively. The shapes of the sides more clearly illustrate the configuration that is used to tightly package a plurality of sensor in a multi-parameter sonde. A first flat-faced surface 530 terminates at the first inner edge 460. A second flat-faced surface 540 terminates at the second inner edge 470. One or more additional sensors (see, e.g., FIG. 3A-3B, sensors 20a 20b), may be used in combination with similarly shaped surfaces with a wiper 180 and rotatable drive shaft 182, and contained within a sensor guard 170 having sensor volume 173 (see, e.g., FIG. 2)

Figure 7A:
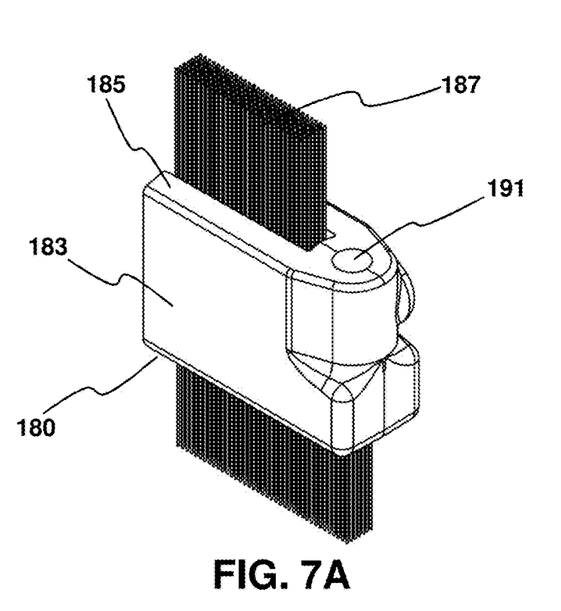
FIG. 7A-7D are illustrations of a wiper that may be connected to the cleanable conductivity sensor for cleaning to improve sensor reliability and increase sensor longevity.
Figure 7B:
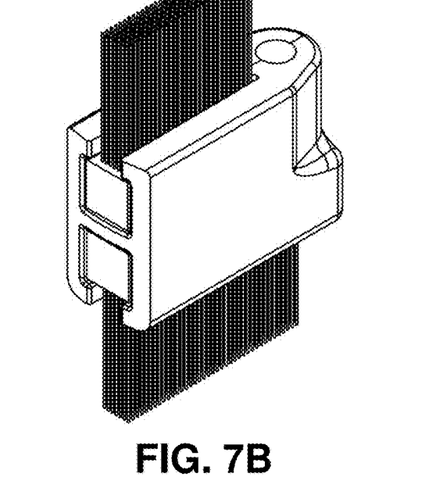
Figure 7C:
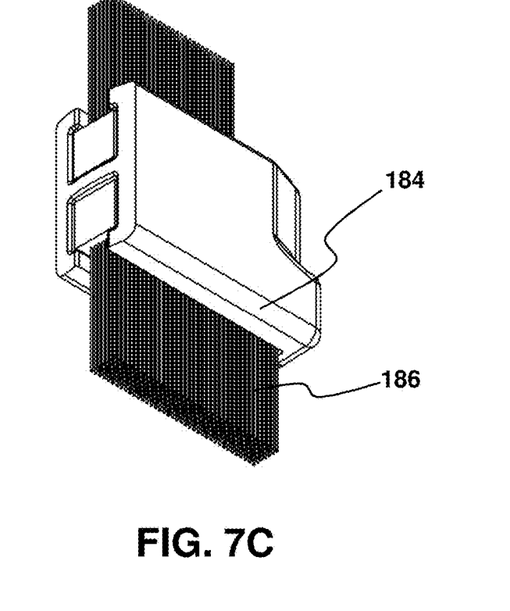
Figure 7D:
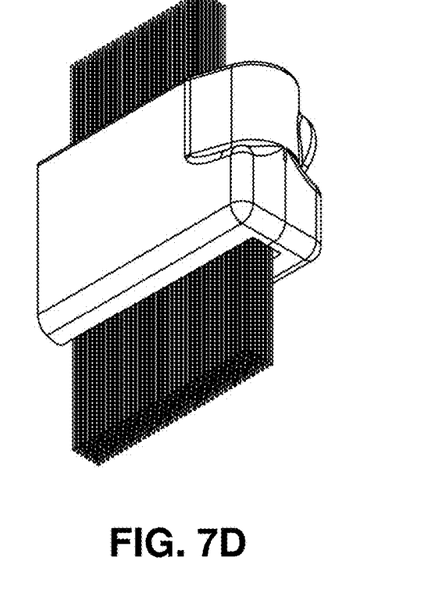

FIG. 7A-7D are views of a wiper 180 detached from the sonde, more specifically from a drive shaft of the sonde. The wiper may have a central body 183 with a downward-facing surface 184 (FIG. 7C) and an upward-facing surface 185 (FIG. 7A). A lower wiper 186 and an upper wiper 187 may connect to opposite surfaces for cleaning a distal sensing surface and an inward-facing surface of the sonde. In an aspect, the wipers may be brushes. The brushes may be configured to provide maximum cleaning area, with the brushes that clean the distal sensing surface cleaning a smaller overall area due to the presence of a drive shaft 182 terminating in a distal end 181 that is receivably positioned in a receiving passage 191 on the wiper 180.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every combination of elements described or exemplified herein can be used to practice the invention, unless otherwise stated.

Whenever a range is given in the specification, for example, a size range, an angle range, or a time or a number range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A cleanable conductivity sensor comprising:
   a substantially planar distal sensing end comprising:
   a vertex region;
   a first inner end edge extending from said vertex region to a first inner end point;
   a second inner end edge extending from said vertex region to a second inner end point, wherein said first inner end edge and said second inner end edge extend in directions to define a vertex angle;
   an outer end edge that extends between said first inner end point and said second inner end point;
   a first flat-faced surface that terminates at the first inner edge;
   a second flat-faced surface that terminates at the second inner edge; and
   a plurality of electrodes, each having a distal electrode end positioned at or proximate to said distal sensing end to measure conductivity and wherein said distal electrode ends of said plurality of electrodes and said distal sensing end together form a substantially planar surface configured for cleaning by a wiper motion along said substantially planar surface.

2. The cleanable conductivity sensor of claim 1, further comprising an outer fin extending from said distal sensing end and positioned adjacent to at least a portion of said outer end edge to define a conductivity measurement cell volume.

3. The cleanable conductivity sensor of claim 2, wherein said outer fin has a fin outer-facing surface positioned within 3 mm of said outer end edge.

4. The cleanable conductivity sensor of claim 3, wherein said fin outer-facing surface extends continuously from at least a portion of said outer end edge to form a continuous outer-facing surface.

5. The cleanable conductivity sensor of claim 2, further comprising an inner fin extending from said distal sensing end, wherein said outer fin and said inner fin are separated from each other by a fin separation distance to define said conductivity measurement cell volume, wherein said outer fin and said inner fin have a laterally-directed shape that corresponds to a shape of said outer end edge.

6. The cleanable conductivity sensor of claim 5, wherein said outer end edge has a curved shape, wherein said curved shape is a portion of a circle.

7. The cleanable conductivity sensor of claim 6, wherein said outer end edge has a radius of curvature that is greater than or equal to 1 cm and less than or equal to 20 cm and said vertex angle is 45°.

8. The cleanable conductivity sensor of claim 5, having an outer fin height and an inner fin height, wherein said outer fin height is equal to said inner fin height.

9. The cleanable conductivity sensor of claim 5, having an outer fin height and an inner fin height, wherein said outer fin height is greater than said inner fin height.

10. The cleanable conductivity sensor of claim 5, having an outer fin surface area and an inner fin surface area, wherein:
    said outer fin surface area is greater than or equal to $2$ $cm^2$ and less than or equal to $8$ $cm^2$; and said inner fin surface area is greater than or equal to 0.3 cm$^2$ and less than or equal to 2 cm$^2$.

11. The cleanable conductivity sensor of claim 5, wherein said fin separation distance is greater than or equal to 0.5 cm and less than a length of said first or second inner end edge.

12. The cleanable conductivity sensor of claim 2, wherein said outer fin dimensions are selected to provide an electric field in said conductivity measurement cell volume that is independent of presence or absence of a sensor guard that encloses said distal sensing end.

13. The cleanable conductivity sensor of claim 2, wherein:
said electrodes are separated from an inner surface of said outer fin by a fin-electrode separation distance;
said outer fin has an outer fin height; and
a ratio of said outer fin height to said fin-electrode separation distance is greater than or equal to 2.4.

14. The cleanable conductivity sensor of claim 2, having an outer fin height that is greater than or equal to 1 mm and less than or equal to 5 cm.

15. The cleanable conductivity sensor of claim 2, further comprising a sensor guard having a plurality of openings to surround said distal sensing end and said outer fin.

16. The cleanable conductivity sensor of claim 15 wherein said outer fin is adjacent to an inner surface of said sensor guard and said sensor guard comprises one or more fluid sample openings for fluid sample introduction from a fluid environment outside said sensor guard to said conductivity measurement cell volume.

17. The cleanable conductivity sensor of claim 16, having a guard separation distance between said outer fin and said sensor guard inner surface that provides a tight-fit that substantially prevents biological growth between said outer fin and said sensor guard inner surface.

18. The cleanable conductivity sensor of claim 17, wherein said guard separation distance is less than 1 mm.

19. The cleanable conductivity sensor of claim 15, having a ratio of conductivity measurement cell volume to a sensor sensing volume that is greater than or equal to 0.0001 and less than or equal to 0.1.

20. The cleanable conductivity sensor of claim 15, wherein said plurality of electrodes are open to a sensor sensing volume.

21. The cleanable conductivity sensor of claim 20, wherein said plurality of electrodes comprise two drive electrodes and two sensing electrodes.

22. The cleanable conductivity sensor of claim 21, further comprising a temperature sensor having a temperature sensing surface that is coincident with or proximal to said distal sensing end.

23. The cleanable conductivity sensor of claim 20, wherein said sensor sensing volume is defined by an inner surface of said sensor guard that encloses said cleanable conductivity sensor, said sensor sensing volume is greater than or equal to 0.5 mL and less than or equal to 100 mL.

24. The cleanable conductivity sensor of claim 23, wherein said conductivity measurement cell volume is defined by an outer fin separation distance from said vertex region, an outer fin height, and a length of said outer fin height.

25. The cleanable conductivity sensor of claim 2, wherein said outer fin minimizes a conductivity interference from objects located outside said conductivity measurement cell volume.

26. The cleanable conductivity sensor of claim 25, wherein said outer fin decreases conductivity interference by at least 50% compared to an equivalent cleanable conductivity sensor without said outer fin.

27. The cleanable conductivity sensor of claim 1, wherein said first inner end edge and said second inner end edge each extend a radial distance from said vertex region, said radial distance selected from a range that is greater than or equal to 1 cm and less than or equal to 20 cm.

28. The cleanable conductivity of sensor of claim 27, wherein said outer end edge is curved.

29. The cleanable conductivity sensor of claim 28, wherein said curve is a portion of a circle.

30. The cleanable conductivity sensor of claim 1, wherein said vertex angle is greater than or equal to 30° and less than or equal to 180°.

31. The cleanable conductivity sensor of claim 1, wherein said distal sensing end has a cleanable surface area that is greater than or equal to 1 cm$^2$ and less than or equal to 20 cm$^2$.

32. The cleanable conductivity sensor of claim 1, wherein said vertex region comprises a notch configured to receive a rotatable drive shaft in a tight-fit configuration.

33. The cleanable conductivity sensor of claim 32 that is part of a multi-parameter sonde and further comprises:
said distal sensing end forms a portion of a circle;
one or more additional sensors, wherein each additional sensor has a distal sensing surface; a first flat-faced inner surface and a second flat-faced inner surface extending from a vertex region that comprises a notch; and a curved outer surface that extends between said one or more additional sensors first flat-faced inner surface and said second flat-faced inner surface;
in combination, said conductivity sensor and said one or more additional sensors form a single continuous sensing surface having a circular outer circumference in a single plane with a central orifice comprising said notches of said vertex regions;
a rotatable drive shaft positioned in said central orifice;
a wiper operably connected to said rotatable drive shaft and in rotatable contact with said single continuous sensing surface for cleaning a sensor portion of said single continuous sensing surface during use and a cleanable surface area of said cleanable conductivity sensor; and
a sensor guard having a sensor volume that contains said continuous sensing surface and wiper.

34. The cleanable conductivity sensor of claim 33, wherein said wiper comprises:
a central body having a downward-facing surface and an upward facing surface;
a lower wiper connected to said downward-facing surface for rotatably contacting said sensor portion of said single continuous sensing surface;
an upper wiper connected to said upward-facing surface for rotatably contacting a downward-facing surface of said sensor guard; and
wherein said lower wiper has a lateral dimension that corresponds to an outer fin separation distance and said upper wiper has a lateral dimension to rotatably contact substantially all of said sensor guard downward-facing surface.

35. The cleanable conductivity sensor of claim 33, wherein the one or more additional sensors are selected from the group consisting of: a dissolved oxygen sensor, oxygen-reduction potential sensor, pH sensor, pressure sensor, turbidity sensor, ion sensor, temperature sensor, and sensor blank.

36. The cleanable conductivity sensor of claim 1, wherein said distal sensing end has a surface shape that is a portion of a circle having a ratio of cleanable surface area to distal sensing end surface area that is greater than or equal to 80%.

37. The cleanable conductivity sensor of claim 1, wherein said substantially planar surface configured for cleaning by the wiper motion facilitates long-term, high-fidelity conductivity sensing without having to remove said cleanable conductivity sensor from a measurement environment and/or without active maintenance.

38. The cleanable conductivity sensor of claim 37, having a measurement accuracy that is within 0.5% for an operating time of at least six months without active maintenance.

39. A method of making a liquid conductivity measurement comprising the steps of:
    providing a multi-parameter sonde comprising a cleanable conductivity sensor of claim 1 and at least one additional sensor, wherein active sensing elements of the sensors are coincident with a single continuous distal sensing surface;
    rotably connecting a wiper to said single continuous distal sensing surface, including a cleanable conductivity sensor portion defined by an outer fin extending from said distal sensing end and positioned adjacent to at least a portion of said outer end edge;
    enclosing the single continuous distal sensing surface and the wiper in a sensor guard having one or more openings;
    inserting the multi-parameter sonde into a liquid environment;
    periodically rotating the wiper over the single continuous distal sensing surface to clean the single continuous distal sensing surface without removing the multi-parameter sonde from the liquid environment; and
    measuring a conductivity parameter with the conductivity sensor,
thereby making an accurate conductivity reading in the liquid environment.

40. The method of claim 39, further comprising the step of storing the wiper in a stored position that does not interfere with a sensor reading of the conductivity sensor or any of the other sensors.

41. The method of claim 39, wherein a performance of said conductivity sensor performance is independent of a position of said one or more openings relative to said conductivity sensor.

42. The method of claim 39, wherein the periodically rotating step is automated and occurs by a user-defined time or in response to a fouling signal from the multi-parameter sonde.

* * * * *